(12) United States Patent
Pradier et al.

(10) Patent No.: US 8,772,322 B2
(45) Date of Patent: Jul. 8, 2014

(54) SYNERGISTIC PRESERVATIVE COMPOSITIONS

(75) Inventors: Gilles Pradier, Quincy-Voisins (FR); Alain Girault, Epinac (FR); Willem Anker, Ellerbek (DE); Christophe Amyot, Paris (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/635,118

(22) PCT Filed: Mar. 14, 2011

(86) PCT No.: PCT/US2011/028353
§ 371 (c)(1), (2), (4) Date: Dec. 20, 2012

(87) PCT Pub. No.: WO2011/115912
PCT Pub. Date: Sep. 22, 2011

(65) Prior Publication Data
US 2013/0131130 A1    May 23, 2013

Related U.S. Application Data

(60) Provisional application No. 61/313,947, filed on Mar. 15, 2010.

(51) Int. Cl.
*A61K 31/428* (2006.01)
(52) U.S. Cl.
USPC .......................................................... 514/373

(58) Field of Classification Search
None
See application file for complete search history.

(56) References Cited

U.S. PATENT DOCUMENTS

| | | | | |
|---|---|---|---|---|
| 4,661,503 A | * | 4/1987 | Martin et al. | 514/372 |
| 4,906,651 A | * | 3/1990 | Hsu | 514/372 |
| 5,585,033 A | * | 12/1996 | Tsao et al. | 514/373 |
| 2009/0191383 A1 | * | 7/2009 | Kluge et al. | 428/195.1 |
| 2009/0325965 A1 | | 12/2009 | Annis et al. | |
| 2012/0164203 A1 | * | 6/2012 | Premachandran et al. | 424/408 |
| 2013/0045241 A1 | * | 2/2013 | Premachandran et al. | 424/400 |

OTHER PUBLICATIONS

PCT, International Search Report, International Application No. PCT/US2011/028353 (mailed Jun. 10, 2011; published Sep. 22, 2011).

* cited by examiner

*Primary Examiner* — San-Ming Hui
*Assistant Examiner* — Jeanmarie Calvillo
(74) *Attorney, Agent, or Firm* — Thompson Hine LLP; William J. Davis

(57) ABSTRACT

A preservative composition comprising: (a) 1,2-Benzisothiazolin-3-one (BIT); (b) 3-Iodo-2-propynyl carbamate (IPBC); and (c) a mixture of 5-Chloro-2-methyl-4-isothiazolin-3-one (CMIT) and 2-Methyl-4-isothiazolm-3-one (MIT).

8 Claims, No Drawings

SYNERGISTIC PRESERVATIVE COMPOSITIONS

FIELD

The present application relates to preservative compositions and more particularly, to synergistic preservative compositions containing a mixture of (a) 1,2-Benzisothiazolin-3-one (BIT); (b) 3-Iodo-2-propynyl carbamate (IPBC); and (c) a mixture of 5-Chloro-2-methyl-4-isothiazolin-3-one (CMIT) and 2-Methyl-4-isothiazolin-3-one (MIT).

BACKGROUND

Commercial use products are generally designed to have a substantial shelf life. The products need to be manufactured at one site, transported possibly over a considerable distance to a depot or other storage facility prior to further transport to a point of sale. The product may then spend considerable time on a retailer's shelf prior to purchase and further storage by the user whether for individual use or use in, for example, a workplace, institution or the like. Storage typically takes place under uncontrolled conditions including considerable variation in temperature.

In order to keep bacterial and fungal growth in such products at an acceptable level it is conventional practice for the products to contain a preservative. Many preservatives are available. The appropriate preservative has to be selected with regard to its efficacy and its acceptability in the product.

SUMMARY

The present application relates to preservative compositions containing: (a) 1,2-Benzisothiazolin-3-one (BIT); (b) 3-Iodo-2-propynyl carbamate (IPBC); and (c) a mixture of 5-Chloro-2-methyl-4-isothiazolin-3-one (CMIT) and 2-Methyl-4-isothiazolin-3-one (MIT).

In accordance with particular embodiments of the present invention, the composition comprises from about 1-20% BIT. In accordance with other embodiments of the present invention, the composition comprises from about 0.5-30% IPBC, and in still other embodiments, the composition comprises from about 0.01-1.5% CMIT/MIT.

DETAILED DESCRIPTION

The present application relates to preservative compositions and, more particularly, to preservative compositions comprising a mixture of (a) 1,2-Benzisothiazolin-3-one (BIT); (b) 3-Iodo-2-propynyl carbamate (IPBC); and (c) a mixture of 5-Chloro-2-methyl-4-isothiazolin-3-one (CMIT) and 2-Methyl-4-isothiazolin-3-one (MIT).

The term "comprising" encompasses the more restrictive terms "consisting essentially of" and "consisting of."

All percentages, ratios and proportions used herein are by weight unless otherwise specified.

In accordance with certain aspects of the present invention, the CMIT and MIT may be provided as a blend. A blend of 75% CMIT and 25% MIT is very effective against bacteria, fungi and algae. Other blends can also be used, such as 90%-10% CMIT and 10%-90% MIT, more particularly 70-80% CMIT and 20-30% MIT.

Preservative compositions in accordance with certain aspects of the present invention contain no formaldehyde. In accordance with certain aspects of the present invention, the preservative compositions are formulated as solutions in water. In accordance with other aspects of the present invention, the preservative composition can be formulated as solutions in solvents such as alcohols, glycols, glycol esters, glycol ethers, polyethylene glycols, polypropylene glycols, and mixtures thereof. Furthermore, non-polar solvents may also be used in accordance with particular embodiments of the present invention. Mixtures of any of these solvents, including water, can also be utilized. Furthermore, various other conventional additives may be employed, such as surfactants, dispersing agents, corrosion inhibitors, and the like.

In addition to the specific biocides (BIT, IPBC, and CMIT/MIT), the preservative composition may contain one or more other biocidal substances. Non-limiting examples of biocidal substances that can be included in the preservative composition are disclosed in U.S. Pat. No. 6,361,788, the contents of which are hereby incorporated by reference.

The preservative compositions described herein are useful in the formulation of household products, industrial products, etc. The preservative composition may be used as an in-can preservative to protect different industrial products, e.g. emulsion paints, adhesives, resins, glues, dispersions and emulsions, cleaning and household products, and water based preparations, against microbial deterioration.

The composition described herein gives a fast speed of kill as well as a long lasting activity against microorganisms like bacteria, fungi and algae.

The composition can be delivered as a powder, dispersion or clear liquid.

Typically, the preservative composition is present in an amount of about 0.01 to 30% by weight of the product, more particularly from about 0.05 to 4% by weight of the product, in certain cases, from about 0.1 to 2%.

The Following examples illustrate the invention.

Example 1

This example shows the synergistic effect of the three essential active components in the biocide composition of the invention.

In this context Synergy is defined as the effect of 2 or more actives being greater than the sum of each active alone.

Synergy is determined from combination studies of the different actives according to the method of calculation put forward by F. C. Kull et al, Applied Microbiology, 9:538 (1961):

$$\text{Synergy Index (SI)} = Q_a/Q_A + Q_b/Q_B$$

Where $Q_a$=concentration of component A in the biocide composition showing the desired effect (e.g. no growth of microorganisms)

$Q_A$=concentration of component A as single component showing the desired effect $Q_b$=concentration of component B in the biocide composition showing the desired effect and $Q_B$=concentration of component B as single component showing the desired effect For a system consisting of three active components the synergy index is calculated by the formula:

$$\text{Synergy Index (SI)} = Q_a/Q_A + Q_b/Q_B + Q_c/Q_C$$

Synergy in a composition then exists when the synergy index is less than 1.

In this example synergy is shown against the microorganism *Staphylococcus aureus* (ATCC 6538). For this purpose MIC values were determined for each individual active as well as for different combinations of the 3 actives. MIC (Minimum Inhibitory Concentration) defines the lowest concentration level of a substance to inhibit the growth of a given organism.

Hence aqueous mixtures were prepared with various concentrations of

Component A=3-Iodo-2-propynyl carbamate (IPBC)

Component B=1,2-Benzisothiazolin-3-one (BIT)

Component C=a mixture of 5-Chloro-2-methyl-4-isothiazolin-3-one and 2-Methyl-4-isothiazolin-3-one (CMIT/MIT).

Subsequently the activity of these mixtures were tested against *Staphylococcus aureus*.

The cell density of *S. aureus* was 10*5 cells/ml. The incubation time was 24 hr at 32° C.

TSB (Tryptic Soy Broth Agar) was used as nutrient medium.

Table 1 shows the concentrations of each active used in the test as well as whether growth of the microorganism took place (symbol "+") or not (symbol "−").

In this way the table represents the MIC value for each tested combination.

TABLE 1

MIC values for *S. aureus* (ATCC#6538) at an incubation time of 24 hours

| IPBC concentration (ppm) | BIT concentration (ppm) | | | | | | | | | | |
|---|---|---|---|---|---|---|---|---|---|---|---|
| | 12.5 | 6.25 | 3.12 | 1.56 | 0.78 | 0.39 | 0.19 | 0.1 | 0.05 | 0.03 | 0.01 |
| With 0.37 ppm CMIT/MIT | | | | | | | | | | | |
| 62.5 | − | − | − | − | − | − | − | − | − | − | − |
| 31.2 | − | − | − | − | − | − | − | − | − | − | − |
| 15.6 | − | − | − | − | − | − | − | − | − | − | − |
| 7.8  | − | − | − | − | + | + | + | + | + | + | + |
| 3.9  | − | − | − | − | + | + | + | + | + | + | + |
| 1.95 | − | − | − | − | + | + | + | + | + | + | + |
| With 1.5 ppm CMIT/MIT | | | | | | | | | | | |
| 62.5 | − | − | − | − | − | − | − | − | − | − | − |
| 31.2 | − | − | − | − | − | − | − | − | − | − | − |
| 15.6 | − | − | − | − | − | − | − | − | − | − | − |
| 7.8  | − | − | − | − | − | − | − | − | − | − | − |
| 3.9  | − | − | − | − | − | − | + | + | + | + | + |
| 1.95 | − | − | − | − | − | + | + | + | + | + | + |
| 0.98 | − | − | − | − | − | + | + | + | + | + | + |
| 0.49 | − | − | − | − | − | + | + | + | + | + | + |
| Without CMIT/MIT | | | | | | | | | | | |

| IPBC concentration (ppm) | 12.5 | 6.25 | 3.12 | 1.56 | 0.78 | 0.39 | 0.19 | 0.1 | 0.05 | 0.03 | 0.01 | 0 |
|---|---|---|---|---|---|---|---|---|---|---|---|---|
| 62.5 | − | − | − | − | − | − | − | − | − | − | − | − |
| 31.2 | − | − | − | − | − | − | − | − | − | − | − | − |
| 15.6 | − | − | − | − | − | − | − | − | − | − | − | − |
| 7.8  | − | − | − | − | − | + | + | + | + | + | + | + |
| 3.9  | − | − | − | − | + | + | + | + | + | + | + | + |
| 1.95 | − | − | − | + | + | + | + | + | + | + | + | + |
| 0.98 | − | − | − | + | + | + | + | + | + | + | + | + |
| 0    | − | − | − | + | + | + | + | + | + | + | + |   |

Single actives only (to determine $Q_A$, $Q_B$ and $Q_C$)

| BIT concentration (ppm) | 100 | 50 | 25 | 12.5 | 6.25 | 3.12 |
|---|---|---|---|---|---|---|
|   | − | − | − | − | − | + |
| IPBC concentration (ppm) | 125 | 62.5 | 31.2 | 15.6 | 7.8 | 3.9 |
|   | − | − | − | − | + | + |
| CIT/MIT concentration (ppm) | 48 | 24 | 12 | 6 | 3 | 1.5 |
|   | − | − | − | − | − | + |

Based on the information from Table 1 the Synergy Index (SI) is calculated for this test series and shown in Table 2.

TABLE 2

Calculation of the synergy index for *S. aureus* (ATCC#6538) at an incubation time of 24 hours ($Q_A$ = 15.6 ppm, $Q_B$ = 6.25 ppm, $Q_c$ = 3 ppm)

| MIC | | | Total con. (ppm) | Concentration | | | Synergy |
|---|---|---|---|---|---|---|---|
| IPBC con. $Q_a$ (ppm) | BIT con. $Q_b$ (ppm) | CMIT/MIT con. $Q_c$ (ppm) | IPBC + BIT + CMIT/MIT ($Q_a + Q_b + Q_c$) | IPBC (% by wt) | BIT (% by wt) | CMIT/MIT (% by wt) | Index SI = $Q_a/Q_A + Q_b/Q_B + Q_c/Q_C$ |
| 7.8 | 1.56 | 0.37 | 9.73 | 80.16% | 16.03% | 3.80% | 0.87 |
| 3.9 | 1.56 |      | 5.83 | 66.90% | 26.76% | 6.35% | 0.62 |

TABLE 2-continued

Calculation of the synergy index for *S. aureus* (ATCC#6538) at an incubation time of 24 hours ($Q_A$ = 15.6 ppm, $Q_B$ = 6.25 ppm, $Q_c$ = 3 ppm)

| MIC | | | Total con. (ppm) | Concentration | | | Synergy |
|---|---|---|---|---|---|---|---|
| IPBC con. $Q_a$ (ppm) | BIT con. $Q_b$ (ppm) | CMIT/MIT con. $Q_c$ (ppm) | IPBC + BIT + CMIT/MIT ($Q_a + Q_b + Q_c$) | IPBC (% by wt) | BIT (% by wt) | CMIT/MIT (% by wt) | Index SI = $Q_a/Q_A$ + $Q_b/Q_B$ + $Q_c/Q_C$ |
| 1.95 | 1.56 | | 3.88 | 50.26% | 40.21% | 9.54% | 0.50 |
| 7.8 | 0.01 | 1.5 | 9.31 | 83.78% | 0.11% | 16.11% | 1.00 |
| 3.9 | 0.39 | | 5.79 | 67.36% | 6.74% | 25.91% | 0.81 |
| 1.95 | 0.78 | | 4.23 | 46.10% | 18.44% | 35.46% | 0.75 |
| 0.98 | 0.78 | | 3.26 | 30.06% | 23.93% | 46.01% | 0.69 |
| 0.49 | 0.78 | | 2.77 | 17.69% | 28.16% | 54.15% | 0.66 |
| 7.8 | 0.78 | 0 | 8.58 | 90.91% | 9.09% | 0 | 0.75 |
| 3.9 | 1.56 | | 5.46 | 71.43% | 28.57% | 0 | 0.75 |

It can be seen from Table 2 that for *Staphylococcus aureus* the optimum synergy (SI is 0.50) is given for a formulation with IPBC:BIT:CMIT/MIT≈5:4:1.

Example 2

In this example synergy is shown against the microorganism *Pseudomonas aeruginosa* (ATCC 9027).

The test protocol is the same as described under Example 1.

Table 3 shows the MIC values of the tested biocide compositions.

TABLE 3

MIC values for *P. aeruginosa* (ATCC 9027) at an incubation time of 24 hours

With 0.75 ppm CMIT/MIT

| IPBC concentration | BIT concentration (ppm) | | | | | | | | | | |
|---|---|---|---|---|---|---|---|---|---|---|---|
| (ppm) | 200 | 100 | 50 | 25 | 12.5 | 6.25 | 3.12 | 1.6 | 0.78 | 0.39 | 0.19 | 0.1 |
| 500 | − | − | − | − | − | − | − | − | − | − | − | − |
| 250 | − | − | − | − | − | − | − | − | − | − | − | − |
| 125 | − | − | − | − | − | − | + | + | + | + | + | + |
| 62.5 | − | − | − | − | − | − | + | + | + | + | + | + |
| 31.2 | − | − | − | − | − | + | + | + | + | + | + | + |
| 15.6 | − | − | − | − | − | + | + | + | + | + | + | + |
| 7.8 | − | − | − | − | − | + | + | + | + | + | + | + |
| 3.9 | − | − | − | − | − | + | + | + | + | + | + | + |

Without CMIT/MIT

| IPBC concentration | BIT concentration (ppm) | | | | | | | | | | |
|---|---|---|---|---|---|---|---|---|---|---|---|
| (ppm) | 200 | 100 | 50 | 25 | 12.5 | 6.25 | 3.12 | 1.6 | 0.78 | 0.39 | 0.19 |
| 250 | − | − | − | − | + | + | + | + | + | + | + |
| 125 | − | − | − | − | + | + | + | + | + | + | + |
| 62.5 | − | − | − | + | + | + | + | + | + | + | + |
| 31.2 | − | − | − | + | + | + | + | + | + | + | + |
| 15.6 | − | − | − | + | + | + | + | + | + | + | + |
| 7.8 | − | − | − | + | + | + | + | + | + | + | + |

Single actives only (to determine $Q_A$, $Q_B$ and $Q_C$)

| BIT concentration (ppm) | 200 | 100 | 50 | 25 | 12.5 | 6.25 |
|---|---|---|---|---|---|---|
| | − | − | − | + | + | + |
| IPBC concentration (ppm) | 1000 | 500 | 250 | 125 | 62.5 | 31.2 |
| | − | + | + | + | + | + |
| CIT/MIT concentration (ppm) | 12 | 6 | 3 | 1.5 | 0.75 | 0.37 |
| | − | − | − | − | + | + |

In Table 4 the synergy index has been calculated. As can be seen, the lowest synergy index (SI is 0.69) for *Pseudomas aeruginosa* is given for a formulation with IPBC:BIT:CMIT/MIT≈90:9:1.

TABLE 4

Calculation of the synergy index for *P. aeruginosa* at an incubation time of 24 hours
($Q_A$ = 1000 ppm, $Q_B$ = 50 ppm, $Q_C$ = 1.5 ppm)

| MIC | | | Total con. (ppm) | Concentration | | | Synergy Index |
|---|---|---|---|---|---|---|---|
| IPBC con. $Q_a$ (ppm) | BIT con. $Q_b$ (ppm) | CMIT/MIT con. $Q_c$ (ppm) | IPBC + BIT + CMIT/MIT ($Q_a + Q_b + Q_c$) | IPBC (% wt) | BIT (% wt) | CMIT/MIT (% wt) | SI = $Q_a/Q_A$ + $Q_b/Q_B$ + $Q_c/Q_C$ |
| 125 | 6.25 | 0.75 | 132 | 94.70% | 4.73% | 0.57% | 0.75 |
| 62.5 | 6.25 | | 69.5 | 89.93% | 8.99% | 1.08% | 0.69 |
| 31.2 | 12.5 | | 44.45 | 70.19% | 28.12% | 1.69% | 0.78 |
| 15.6 | 12.5 | | 28.85 | 54.07% | 43.33% | 2.60% | 0.77 |
| 7.8 | 12.5 | | 21.05 | 37.05% | 59.38% | 3.56% | 0.76 |
| 3.9 | 12.5 | | 17.15 | 22.74% | 72.89% | 4.37% | 0.75 |
| 125 | 25 | 0 | 150 | 83.33% | 16.67% | 0.00% | 0.63 |

Example 3

In this example synergy is shown against the microorganism *Escherichia coli* (ATCC 8793).
The test protocol is the same as described under Example 1.
Table 5 shows the MIC values of the tested biocide compositions,

TABLE 5

MIC values for *E. coli* (ATCC 8739) at an incubation time of 24 hours

| IPBC concentration (ppm) | BIT concentration (ppm) | | | | | | | | | | |
|---|---|---|---|---|---|---|---|---|---|---|---|
| | 12.5 | 6.25 | 3.12 | 1.56 | 0.78 | 0.39 | 0.19 | 0.1 | 0.05 | 0.03 | 0.01 |
| With 0.19 ppm CMIT/MIT | | | | | | | | | | | |
| 125 | − | − | − | − | − | − | − | − | − | − | − |
| 62.5 | − | − | − | + | + | + | + | + | + | + | + |
| 31.2 | − | − | − | + | + | + | + | + | + | + | + |
| 15.6 | − | − | − | + | + | + | + | + | + | + | + |
| 7.8 | − | − | − | + | + | + | + | + | + | + | + |
| 3.9 | − | − | − | + | + | + | + | + | + | + | + |
| With 0.75 ppm CMIT/MIT | | | | | | | | | | | |
| 125 | − | − | − | − | − | − | − | − | − | − | − |
| 62.5 | − | − | − | − | − | − | − | − | − | − | − |
| 31.2 | − | − | − | − | − | + | + | + | + | + | + |
| 15.6 | − | − | − | + | + | + | + | + | + | + | + |
| 7.8 | − | − | − | + | + | + | + | + | + | + | + |
| 3.9 | − | − | − | + | + | + | + | + | + | + | + |
| Without CMIT/MIT | | | | | | | | | | | |

| IPBC concentration (ppm) | BIT concentration (ppm) | | | | | | | | | |
|---|---|---|---|---|---|---|---|---|---|---|
| | 200 | 100 | 50 | 25 | 12.5 | 6.25 | 3.12 | 1.56 | 0.78 | 0.39 | 0.19 |
| 125 | − | − | − | − | − | − | − | − | − | − |
| 62.5 | − | − | − | − | − | − | + | + | + | + |
| 31.2 | − | − | − | − | − | + | + | + | + | + |
| 15.6 | − | − | − | − | − | + | + | + | + | + |
| 7.8 | − | − | − | − | − | + | + | + | + | + |
| 3.9 | − | − | − | − | − | + | + | + | + | + |
| Single actives only (to determine $Q_A$, $Q_B$ and $Q_C$) | | | | | | | | | | |
| BIT concentration (ppm) | 100 | 50 | 25 | 12.5 | 6.25 | 3.12 | 1.56 |
| | − | − | − | − | − | + | + |

TABLE 5-continued

| MIC values for *E. coli* (ATCC 8739) at an incubation time of 24 hours | | | | | | | |
|---|---|---|---|---|---|---|---|
| IPBC concentration (ppm) | 500 | 250 | 125 | 62.5 | 31.2 | 15.6 | 7.8 |
| | − | − | − | + | + | + | + |
| CIT/MIT concentration (ppm) | 48 | 24 | 12 | 6 | 3 | 1.5 | 0.75 |
| | − | − | − | − | − | + | + |

In Table 6 the synergy index has been calculated. As can be seen, the lowest synergy index (SI is 0.59) for *Escherichia coli* is given for a formulation with IPBC:BIT:CMIT/MIT≈20:16:1.

TABLE 6

Calculation of the synergy index for *E. coli* at an incubation time of 24 hours
($Q_A$ = 125 ppm, $Q_B$ = 6.25 ppm, $Q_C$ = 3 ppm)

| MIC | | | Total con. (ppm) | Concentration | | | Synergy |
|---|---|---|---|---|---|---|---|
| IPBC con. $Q_a$ (ppm) | BIT con. $Q_b$ (ppm) | CMIT/MIT con. $Q_c$ (ppm) | IPBC + BIT + CMIT/MIT ($Q_a + Q_b + Q_c$) | IPBC (% by wt) | BIT (% by wt) | CMIT/MIT (% by wt) | Index SI = $Q_a/Q_A + Q_b/Q_B + Q_c/Q_C$ |
| 62.5 | 1.56 | 0.19 | 64.25 | 97.28% | 2.43% | 0.30% | 0.81 |
| 31.2 | 3.12 | | 34.51 | 90.41% | 9.04% | 0.55% | 0.81 |
| 15.6 | 3.12 | | 18.91 | 82.50% | 16.50% | 1.00% | 0.69 |
| 7.8 | 3.12 | | 11.11 | 70.21% | 28.08% | 1.71% | 0.62 |
| 3.9 | 3.12 | | 7.21 | 54.09% | 43.27% | 2.64% | 0.59 |
| 31.2 | 0.78 | 0.75 | 32.73 | 95.33% | 2.38% | 2.29% | 0.62 |
| 15.6 | 3.12 | | 19.47 | 80.12% | 16.02% | 3.85% | 0.87 |
| 7.8 | 3.12 | | 11.67 | 66.84% | 26.74% | 6.43% | 0.81 |
| 3.9 | 3.12 | | 7.77 | 50.19% | 40.15% | 9.65% | 0.78 |
| 1.95 | 3.12 | | 5.82 | 33.51% | 53.61% | 12.89% | 0.76 |
| 0.98 | 3.12 | | 4.85 | 20.21% | 64.33% | 15.46% | 0.76 |
| 62.5 | 3.12 | 0 | 150 | 83.33% | 16.67% | 0 | 1 |

We claim:

1. A preservative composition comprising:
   (a) 1,2-Benzisothiazolin-3-one (BIT);
   (b) 3-Iodo-2-propynyl carbamate (IPBC); and
   (c) a mixture of 5-Chloro-2-methyl-4-isothiazolin-3-one (CMIT) and 2-Methyl-4-isothiazolin-3-one (MIT), wherein the preservative effect of the preservative composition is greater than the sum of the effect of each of BIT, IPBC, CMIT, and MIT alone.

2. The composition of claim 1 wherein said 1,2-Benzisothiazolin-3-one is present in a total amount of about 1% to 20%.

3. The composition of claim 1 wherein said 3-Iodo-2-propynyl carbamate is present in a total amount of about 0.5% to 30%.

4. A composition of claim 1 wherein said mixture of 5-Chloro-2-methyl-4-isothiazolin-3-one and 2-Methyl-4-isothiazolin-3-one is present in a total amount of about 0.01% to 1.5%.

5. The composition of claim 1 wherein the CMIT and MIT are at a ratio of about 6:4 to 9:1.

6. The composition of claim 1 comprising about 15% (a), about 2.4% (b) and about 0.4% (c).

7. The composition of claim 6 wherein (c) comprises a 3:1 ratio of CMIT and MIT.

8. A method for inhibiting the growth of microorganisms comprising adding a preservative composition in accordance with claim 1 to a product susceptible to growth of microorganisms wherein said composition is added in an amount sufficient to inhibit said growth.

* * * * *